United States Patent
Lightsey

(10) Patent No.: US 10,334,929 B2
(45) Date of Patent: Jul. 2, 2019

(54) HAIR PRODUCT APPLICATION DEVICE

(71) Applicant: The Pro-Motion Group, LLC, Ruffin, SC (US)

(72) Inventor: Larry J. Lightsey, Ruffin, SC (US)

(73) Assignee: The Pro-Motion Group, LLC, Ruffin, SC (US)

( * ) Notice: Subject to any disclaimer, the term of this patent is extended or adjusted under 35 U.S.C. 154(b) by 379 days.

(21) Appl. No.: 15/078,016

(22) Filed: Mar. 23, 2016

(65) Prior Publication Data
US 2017/0020259 A1   Jan. 26, 2017

Related U.S. Application Data

(60) Provisional application No. 62/196,012, filed on Jul. 23, 2015.

(51) Int. Cl.
| | |
|---|---|
| *A45D 7/00* | (2006.01) |
| *A45D 19/02* | (2006.01) |
| *A45D 7/04* | (2006.01) |
| *A47K 7/02* | (2006.01) |
| *A47K 7/03* | (2006.01) |
| *A61K 8/02* | (2006.01) |

(Continued)

(52) U.S. Cl.
CPC ............ *A45D 19/02* (2013.01); *A45D 7/04* (2013.01); *A45D 19/00* (2013.01); *A47K 7/02* (2013.01); *A47K 7/03* (2013.01); *A61K 8/0208* (2013.01); *A61M 35/006* (2013.01); *A61Q 5/02* (2013.01); *A61Q 5/04* (2013.01); *A61Q 5/06* (2013.01); *A61Q 5/12* (2013.01); *A41D 19/0079* (2013.01); *A45D 2007/002* (2013.01); *A45D 2019/005* (2013.01); *A61K 2800/87* (2013.01)

(58) Field of Classification Search
CPC . A45D 7/00; A45D 7/04; A45D 19/00; A45D 19/02; A45D 19/025; A45D 2019/005; A45D 2019/0066; A47K 7/02; A47K 7/03; A61K 8/0208; A61Q 5/02; A61Q 5/04; A61Q 5/06; A61Q 5/12; A47L 13/18; A47L 13/19
See application file for complete search history.

(56) References Cited

U.S. PATENT DOCUMENTS 2,722,706 A * 11/1955 Chopp ............... A41D 19/0055
                                                    15/104.94
3,342,182 A    9/1967 Charos
(Continued)

FOREIGN PATENT DOCUMENTS

CA        2897115        *  7/2013

*Primary Examiner* — Rachel R Steitz
(74) *Attorney, Agent, or Firm* — F. Rhett Brockington

(57) ABSTRACT

A hair product application device for dispensing a hair product composition directly from a glove. The hair product application device generally includes a glove having at least one blister pack containing a hair product composition. The blister pack includes a pocket that holds the hair product composition and is at least partially in contact with an exterior surface of the glove. The pocket has a rupturable membrane and optionally, a backing sheet that is located at least partially on the exterior surface of the glove. The hair product composition is released by rupturing the rupturable membrane of the blister pack by applying an external pressure to the exterior surface of the rupturable membrane or an internal pressure to the pocket using a pneumatic device.

6 Claims, 17 Drawing Sheets

(51) Int. Cl.
*A61F 13/40* (2006.01)
*A45D 19/00* (2006.01)
*A61Q 5/02* (2006.01)
*A61Q 5/04* (2006.01)
*A61Q 5/06* (2006.01)
*A61Q 5/12* (2006.01)
*A41D 19/00* (2006.01)

(56) References Cited

U.S. PATENT DOCUMENTS

| | | |
|---|---|---|
| 3,638,789 A | 2/1972 | Tuszewski |
| 4,122,554 A | 10/1978 | Stager |
| 4,848,246 A | 7/1989 | Rosen |
| 5,096,089 A | 3/1992 | McLaughlin |
| 5,636,406 A | 6/1997 | Strong |
| 5,682,612 A | 11/1997 | Schwarz |
| 5,867,829 A | 2/1999 | Hegoas |
| 6,375,034 B1 | 4/2002 | Corbett |
| 6,513,998 B1 * | 2/2003 | Barry ............... A41D 19/0079 401/196 |
| 6,539,549 B1 | 4/2003 | Peters, Jr. |
| 6,602,493 B2 | 8/2003 | Akhter |
| 7,467,420 B2 | 12/2008 | Ponce |
| 7,665,176 B2 | 2/2010 | Benjamin |
| 7,850,041 B2 | 12/2010 | Amundson |
| 2005/0150784 A1 | 7/2005 | Sanchez |
| 2007/0045135 A1 * | 3/2007 | Berger Sharp ............ A46B 5/04 206/229 |
| 2007/0160547 A1 | 7/2007 | Duffy |
| 2008/0041319 A1 * | 2/2008 | Rasmussen ............ A01K 13/001 119/603 |
| 2011/0306942 A1 * | 12/2011 | Thorpe ................. A45D 34/04 604/289 |
| 2012/0285983 A1 | 11/2012 | Ahlbrand |

* cited by examiner

HAIR PRODUCT APPLICATION DEVICE

CROSS REFERENCE TO RELATED APPLICATIONS

I hereby claim benefit under Title 35, United States Code, Section 119(e) of U.S. provisional patent application Ser. No. 62/196,012 filed Jul. 23, 2015. The 62/196,012 application is currently pending. The 62/196,012 application is hereby incorporated by reference into this application.

STATEMENT REGARDING FEDERALLY SPONSORED RESEARCH OR DEVELOPMENT

Not applicable to this application.

BACKGROUND

Field

Example embodiments in general relate to a hair product application device for applying a hair product composition that is dispensed directly from a glove and more specifically relate to a glove having one or more blister packs that comprise a rupturable membrane that dispenses the hair product composition in response to an internal or external pressure of sufficient force to rupture the membrane.

Related Art

Any discussion of the related art throughout the specification should in no way be considered as an admission that such related art is widely known or forms part of common general knowledge in the field.

In the hair styling industry, conventional disposable gloves are typically utilized to protect the wearer's hands from exposure to dyes and other harmful chemicals that may stain or otherwise damage the skin. There are also numerous gloves designed for use in other industries in which dispensing, spreading, or otherwise dispersing a substance other than the glove material itself may be desirable. Generally, this is accomplished through the use of an absorbent material or pad on the glove that is used to absorb and redistribute a liquid when placed in contact with a substance of appropriate viscosity for absorption and redistribution. While these previously known gloves are suitable for their respective purposes, they are unsuitable for direct dispensing and application of a hair styling product composition onto a glove wearer's or other individual's hair or scalp.

SUMMARY

An example embodiment of the present invention is directed to a hair product application device. The hair product application device includes a hair product application device that includes one or more blister packs containing a hair product disposed on a glove.

There has thus been outlined, rather broadly, some of the features of the hair product application device in order that the detailed description thereof may be better understood, and in order that the present contribution to the art may be better appreciated. There are additional features of the hair product application device that will be described hereinafter and that will form the subject matter of the claims appended hereto. In this respect, before explaining at least one embodiment of the hair product application device in detail, it is to be understood that the hair product application device is not limited in its application to the details of construction or to the arrangements of the components set forth in the following description or illustrated in the drawings. The hair product application device is capable of other embodiments and of being practiced and carried out in various ways. Also, it is to be understood that the phraseology and terminology employed herein are for the purpose of the description and should not be regarded as limiting.

Embodiments of a hair product application device may comprise a glove having a plurality of digit portions with a blister pack disposed on at least one of the digit portions, a dorsal region, or a palmar region of the glove. The blister pack may comprise a pocket at least partially in direct contact with an external surface of the glove, the pocket having a rupturable membrane that contains a hair product composition. The rupturable membrane may be ruptured when exposed to internal or external pressure thereby releasing the hair product composition for use. Alternatively, in some embodiments, the pocket may include a backing sheet that is at least partially in direct contact with the external surface of the glove.

Some embodiments may further comprise a pneumatic device that is in fluid communication with the pocket of the blister pack via a tube such that rupture of the rupturable membrane is exacted by an internal force applied to the pocket by air forced into the pocket from the pneumatic device. The tube may be coupled to the pocket via a bore in the backing sheet and a one-way valve may be in fluid communication with the bore to prevent backflow of hair product composition into the tube and/or pneumatic device. Other embodiments may alternatively utilize a tubular fitting that is coupled to the tube and is in fluid communication with the interior of the pocket via a plurality of outlet ports in the backing sheet.

A removable cover may be present in some embodiments which may be placed over the rupturable membrane to prevent inadvertent and undesired membrane rupture.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

DETAILED DESCRIPTION

Figure 1:
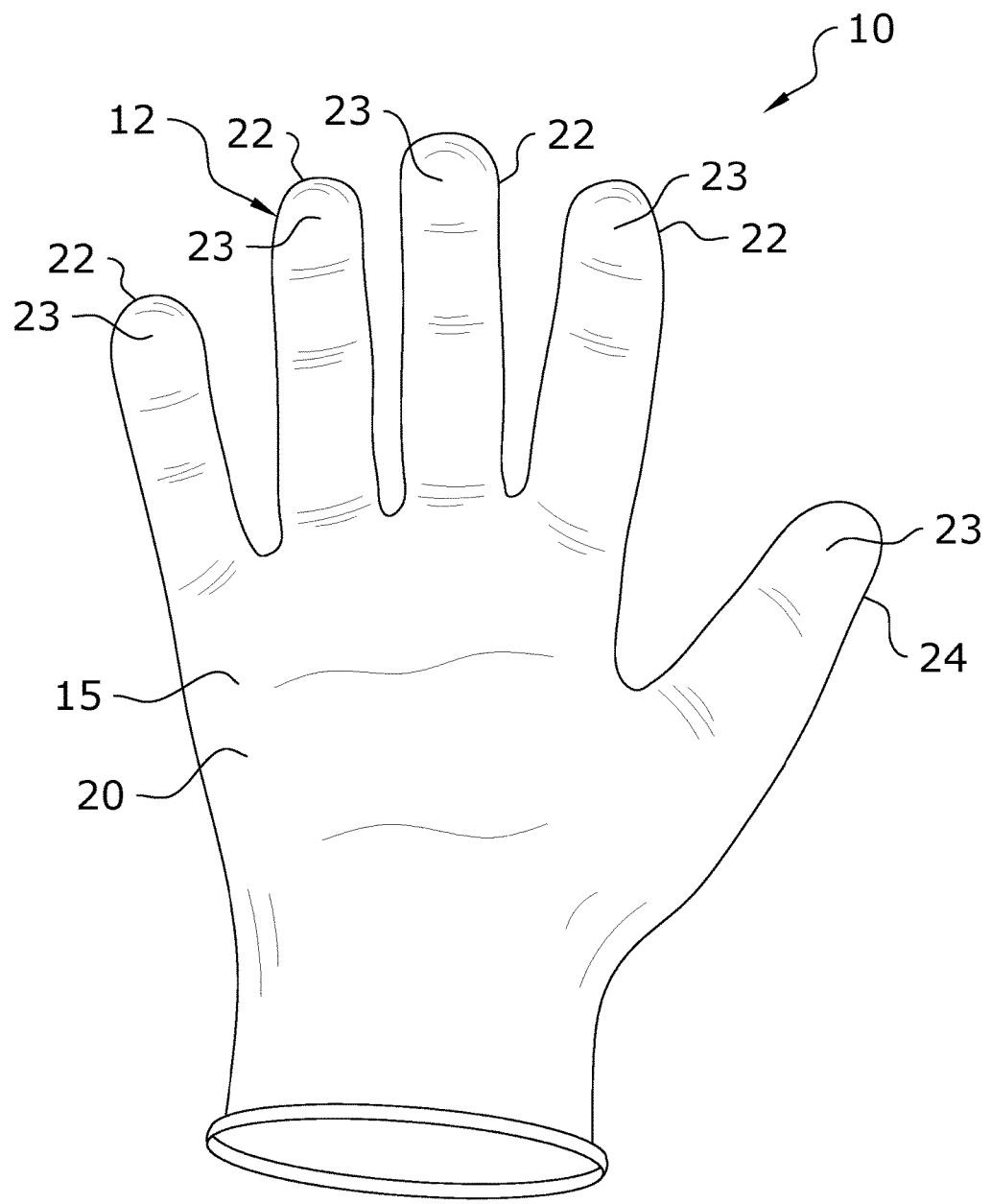
FIG. 1 is a dorsal view of a hair product application device in accordance with an exemplary embodiment.

The detailed description of exemplary embodiments herein makes reference to the accompanying drawings, which show exemplary embodiments by way of illustration and their best mode. While these exemplary embodiments are described in sufficient detail to enable those skilled in the art to practice the inventions, it should be understood that other embodiments may be realized and that logical, chemical and mechanical changes may be made without departing from the spirit and scope of the disclosure. Thus, the detailed description herein is presented for purposes of illustration only and not of limitation. For example, the steps recited in any of the method or process descriptions may be executed in any order and are not necessarily limited to the order presented.

Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact. As used herein, phrases such as "make contact with," "coupled to," "touch," "interface with" and "engage" may be used interchangeably.

The features, structures, or characteristics of the invention described throughout this specification may be combined in any suitable manner in one or more embodiments. For example, the usage of the phrases "example embodiments", "some embodiments" or other similar language refers to the fact that a particular feature, structure, or characteristic described in connection with the embodiment may be included in at least one embodiment of the present invention. Thus, appearances of the phrases "example embodiments", "in some embodiments", "in other embodiments" or other similar language, throughout this specification do not necessarily all refer to the same group of embodiments, and the described features, structures, or characteristics may be combined in any suitable manner in one or more embodiments.

For purposes of description and illustration of the exemplary embodiments disclosed herein, reference(s) to the hand will utilize standard and accepted anatomical terminology, so that standard anatomical positioning of the hand is the baseline with regard to terminology and description. For instance, the palm of the hand may be described as being the anterior surface or region of the hand, and the back of the hand may be described as the posterior of the hand. Also, the terms "palmar" (the palm) and "dorsal" (back of the hand) may also be used. Other terminology that may be used involves description of the fingers and thumb with relation to positioning in a hand covering article, such as a glove. The four fingers each have three (3) phalanges: a proximal phalanx, an intermediate phalanx, and a distal phalanx (bone corresponding to the tip of the finger). The thumb has a proximal phalanx and a distal phalanx, but no intermediate phalanx. These terms are referenced with regard to the positioning of elements of the glove described below, and will become more clear and evident through the examples provided herein.

FIG. 1 provides a dorsal view of an exemplary embodiment of a hair product application device 10. As shown, the hair product application device 10 comprises a glove 12 which may be comprised of any flexible material that is designed to protect the user's hand while being suitable for use with a hair product composition 50. In some embodiments, the glove 12 may be disposable and/or have lint-free, anti-static, or hypo-allergenic properties. The glove 12 comprises a hand portion 20 comprising digit portions 23 which may be more specifically referred to as finger portions 22 and a thumb portion 24.

In accordance to one exemplary embodiment, the glove 12 may be constructed of a fibrous material which carries or otherwise holds a hair product composition 50. The hair product composition 50 may be applied to the glove 12 by coating, spraying, extruding, or any other suitable method of applying a hair product composition 50 to a glove material. The glove 12 may be manufactured so as to be wearable on both the right and left hand of a user, or the glove 12 may also be manufactured as a pair of gloves 12, one to be worn on user's right hand, and another worn on user's left hand. It is desirable that the glove(s) 12 be packaged in a manner that is convenient for a consumer to carry, store, and use, which will be discussed in further detail with regard to FIGS. 11-12.

Figure 2:
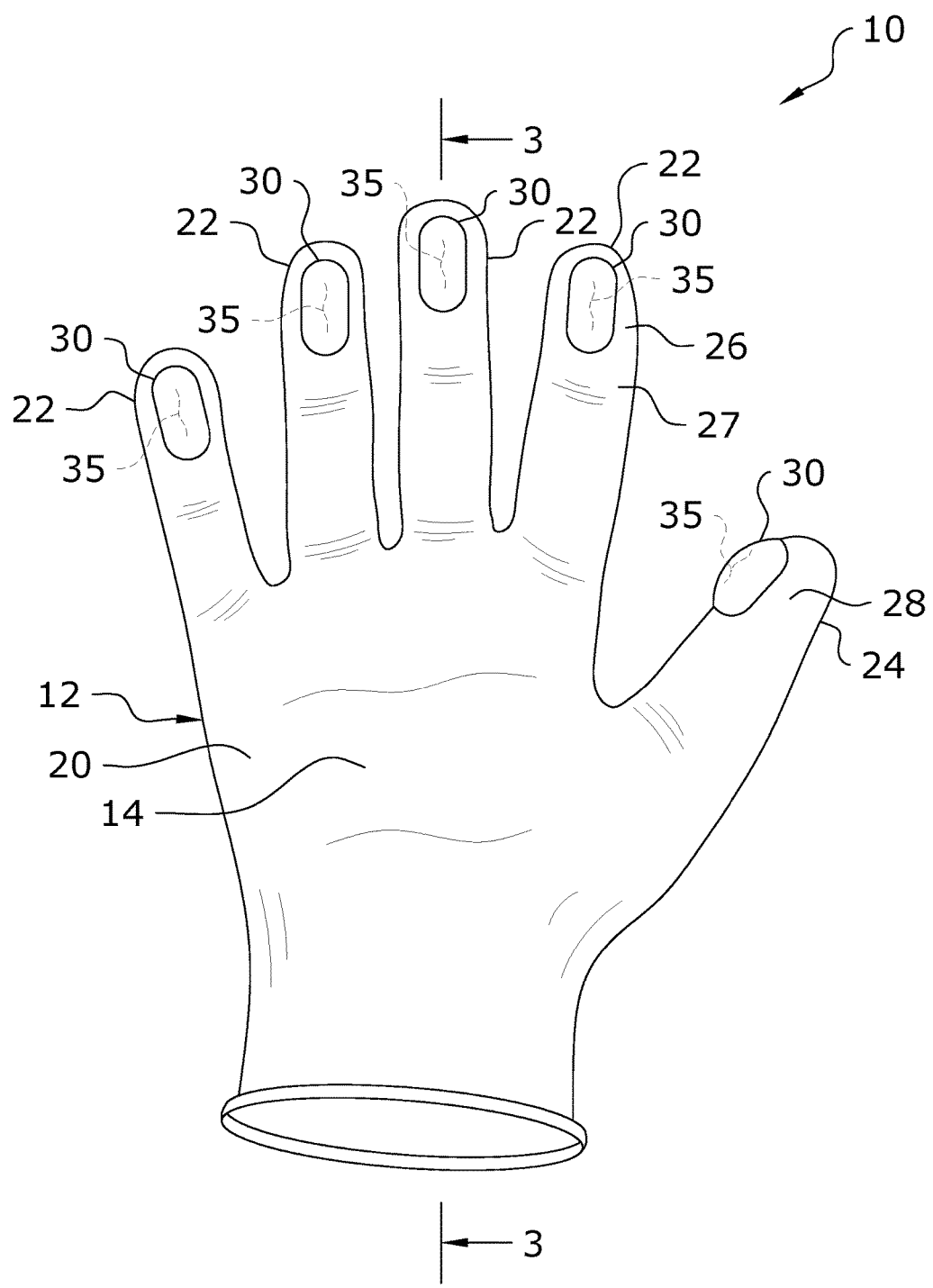
FIG. 2 is a palmar view of a hair product application device in accordance with an exemplary embodiment having a blister pack located on one or more digits of a glove.

FIG. 2 provides a palmar view of the hair product application device 10 in accordance with one embodiment. One or more blister packs 30 containing one or more hair product compositions 50 may be disposed on one or more digit portions 23 of the glove 12. As shown here, blister packs 30 are generally located about the anterior distal phalanx region 26 and the anterior intermediate phalanx region 27 of each finger portion 22 and the anterior proximal phalanx region 28 of the thumb portion 24. While FIG. 2 shows one exemplary embodiment, it is contemplated that any number of blister packs 30 may be used and that the placement of one or more blister packs 30 may differ from the positioning shown here to suit the particular use for which the hair product application device 10 is adapted and therefore, one or more blister packs 30 may be located on the palmar region 14, dorsal region 15, or anywhere on one or more digit portions 23 of the glove 12.

As shown here, blister pack 30 comprises a pocket 33 formed by a backing sheet 34 and a rupturable membrane 32. It should be noted, however, that backing sheet 34 is an optional element in all of the embodiments described herein and that pocket 33 may be formed by rupturable membrane 32 and an exterior surface of the glove 13 in any of the disclosed embodiments. The rupturable membrane 32 may be comprised of any suitable material having an appropriate tensile strength to contain a hair product composition 50 in the absence of an internal or external force being applied to the rupturable membrane 32 but that will also allow for ease of rupturing to dispense the hair product composition 50 when the user creates a pressure differential between interior 37 and exterior 38 surfaces of the rupturable membrane 32. In some embodiments, the rupturable membrane 32 may comprise a rupture line 35 comprised of a weaker, thinner, or otherwise more easily rupturable material such that the pressure necessary to rupture the membrane 32 is lessened and dispensing of the hair product composition 50 occurs at a predetermined location of the rupturable membrane 32. It may also be desirable that the rupturable membrane 32 be comprised of a substantially transparent material so that the user can readily identify the hair product composition 50 contained within the blister pack 30.

The backing sheet 34 may be comprised of a flexible material that does not impede the user's ability to move or flex the digit or hand portion on which the blister pack 30 is located. In some embodiments, the backing sheet 34 may be comprised of multiple layers of the same or different materials. At least a portion of the backing sheet 34 is in direct contact with an exterior surface 13 of the area of the glove 12 upon which the blister pack 30 is disposed. The backing sheet 34 may be coupled to the exterior surface 13 of the glove 12 using any appropriate attachment technique such as for example, using an adhesive or heat-sealing method, and similarly, the rupturable membrane 32 may be coupled to the backing sheet 34 with these or other suitable methods.

Figure 3A:
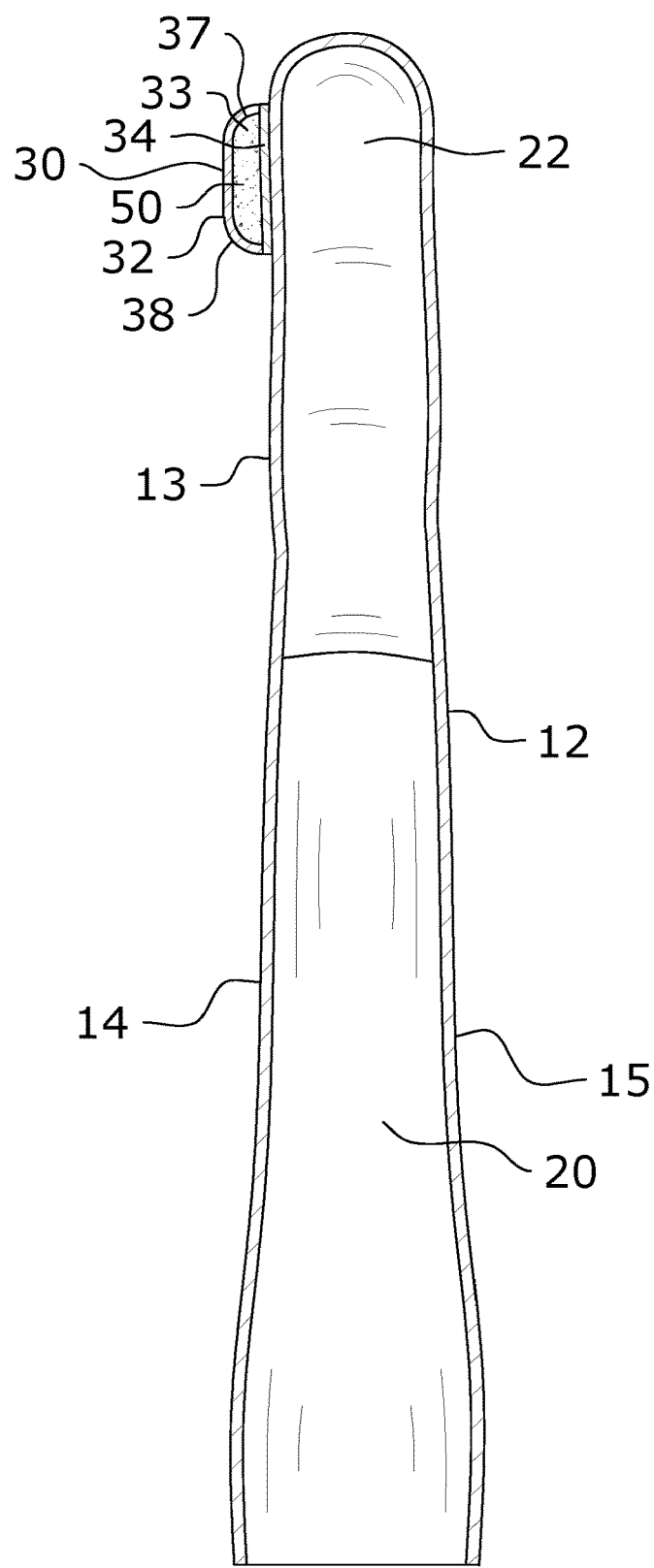
FIGS. 3A-C are cross-sectional views of a glove finger of a hair product application device in accordance with the embodiment of FIG. 2.
Figure 3B:
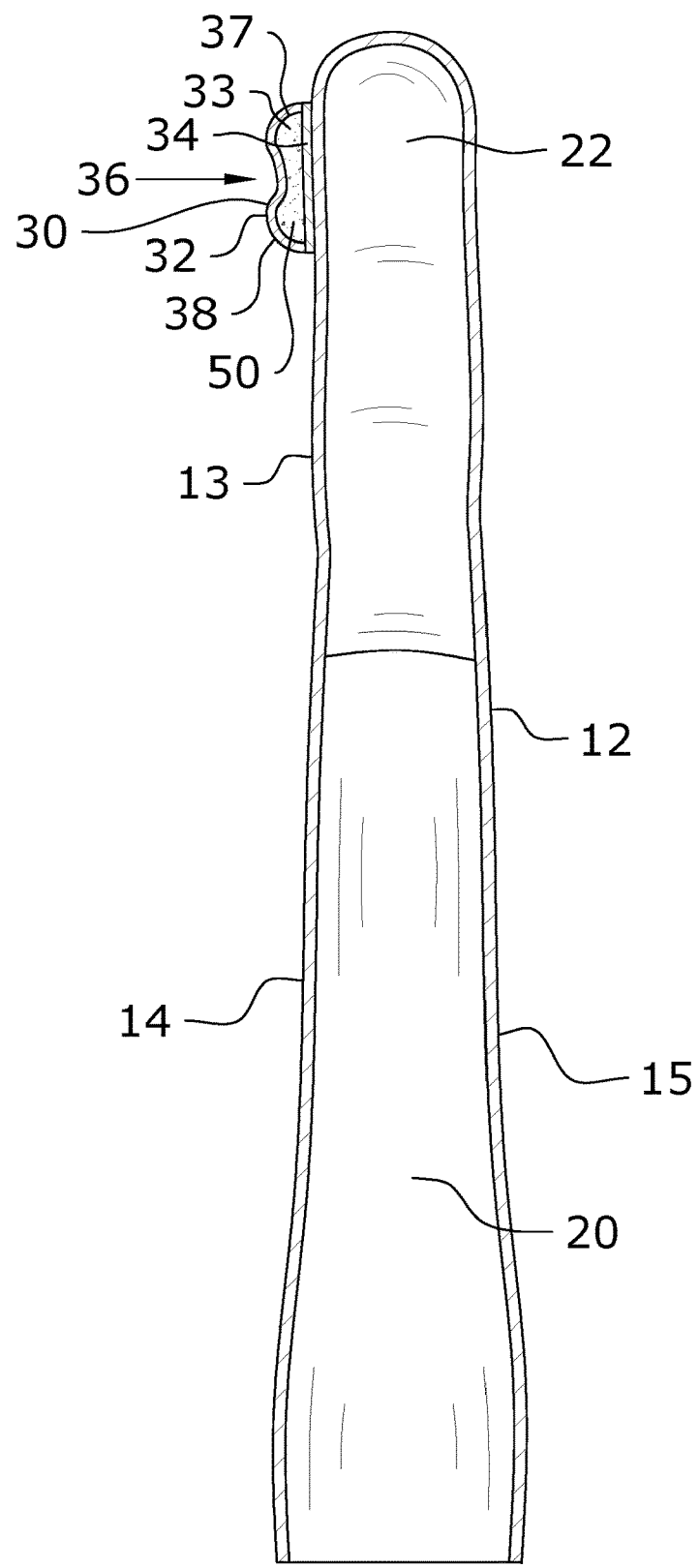
Figure 3C:
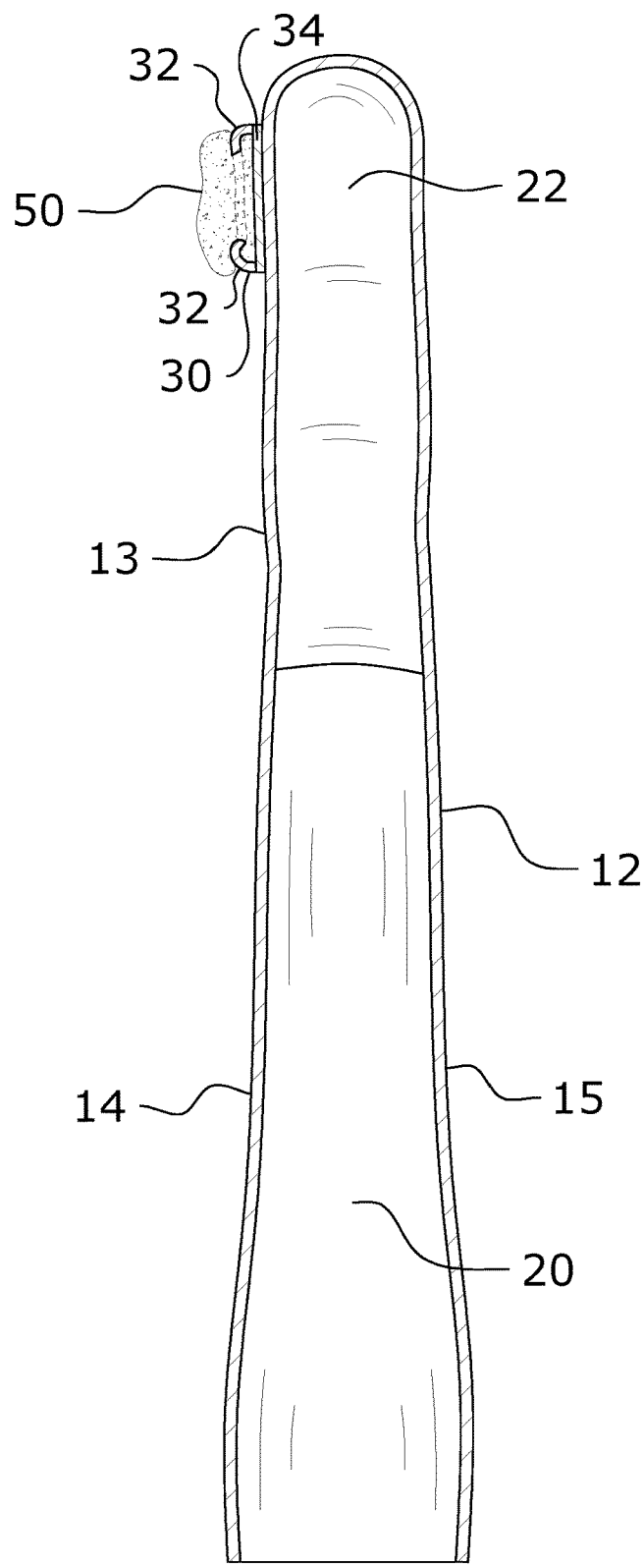

FIGS. 3A-C provide a cross-sectional view of a finger portion 22 of the glove 12 having a blister pack 30 disposed on its anterior side. Backing sheet 34 is at least partially in direct contact with the exterior surface 13 of the glove 12 and initially, in FIG. 3A, the hair product composition 50 is contained within the pocket 33 formed by the backing sheet 34 and the rupturable membrane 32. When an external force 36 is applied in FIG. 3B, a pressure differential is created between the interior 37 and exterior 38 surfaces of the rupturable membrane 32, thereby causing the membrane 32 to rupture and dispense the hair product composition 50 as shown in FIG. 3C. Once the hair product composition 50 has been dispensed, the user may easily apply the dispensed product to the user's or another's hair or scalp.

Figure 3D:
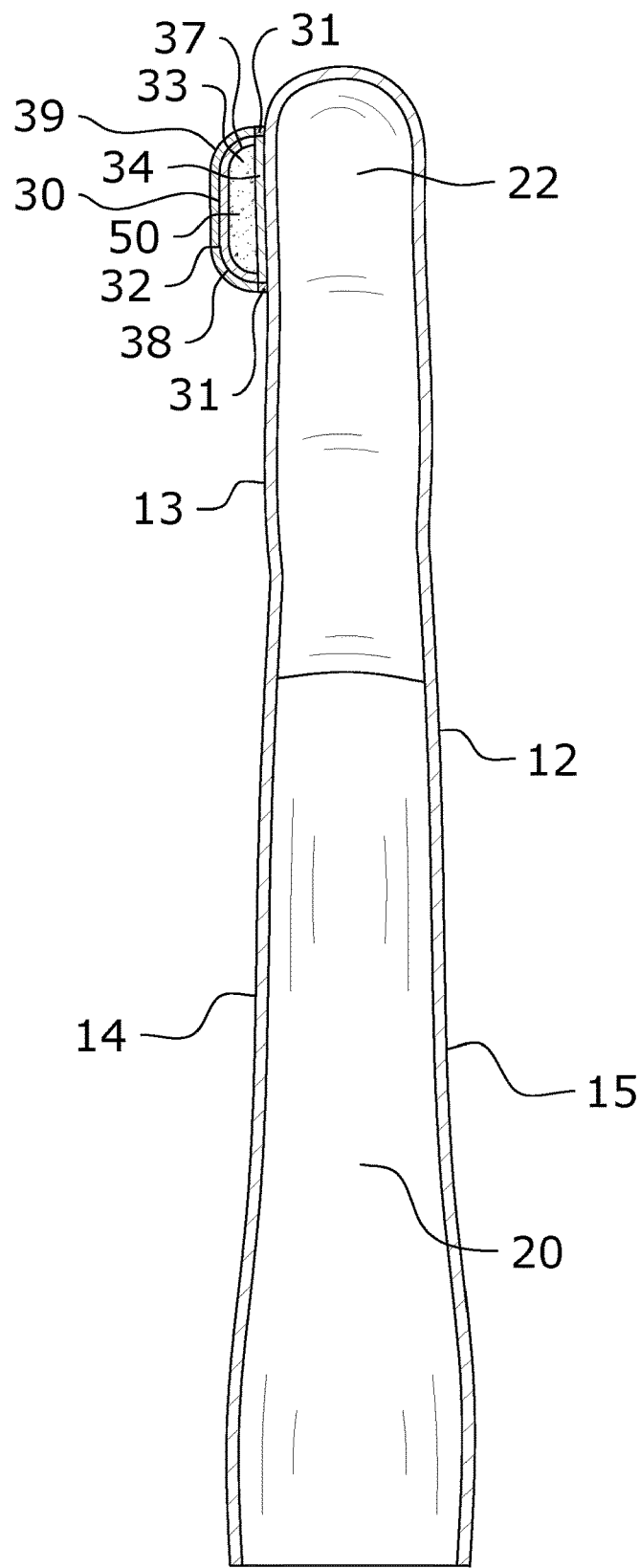
FIG. 3D is a cross-sectional view of a glove finger of the hair product application device in accordance with the embodiment of FIG. 2 comprising a removable cover.

To protect the rupturable membrane 32 from inadvertent or undesired rupture, a removable cover 39 or cap may be placed over the rupturable membrane 32 when the hair product application device 10 is not in use. The removable cover 39 may couple to the blister pack 30 by fitting into a groove or other recess in the backing sheet 34 or may be adhered, such as by non-limiting example, using a pressure-sensitive acrylate adhesive to adhere the removable cover 39 to a releasable liner 31 located at or about the perimeter of the rupturable membrane 32 as shown in FIG. 3D. While the removable cover 39 is shown relative to the embodiment of FIGS. 3A-D, it is to be understood that the removable cover 39 may be used in conjunction with any of the embodiments described herein.

Figure 4:
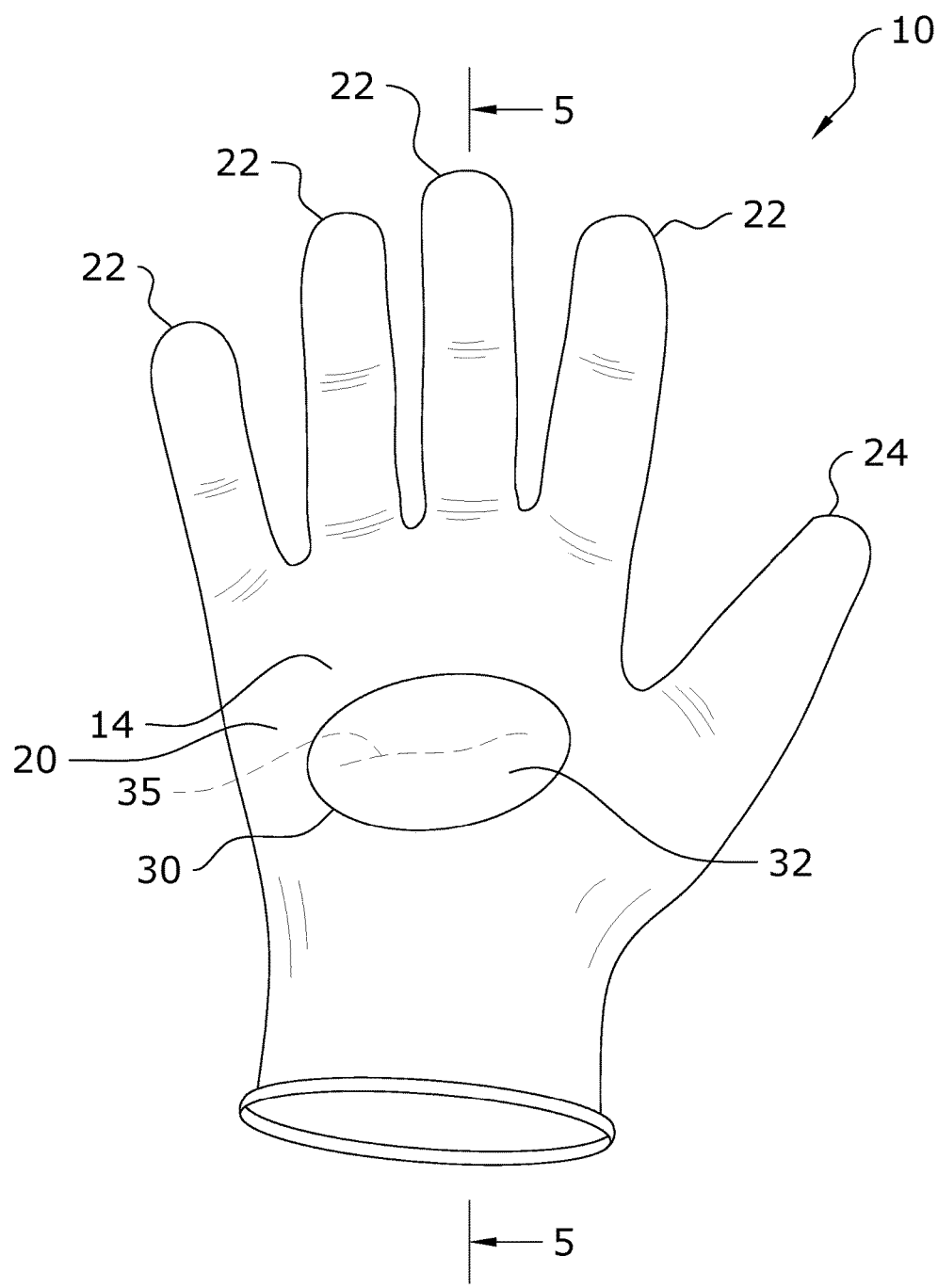
FIG. 4 is a palmar view of a hair product application device in accordance with an exemplary embodiment having one or more blister packs located on a palm of a glove.
Figure 5:
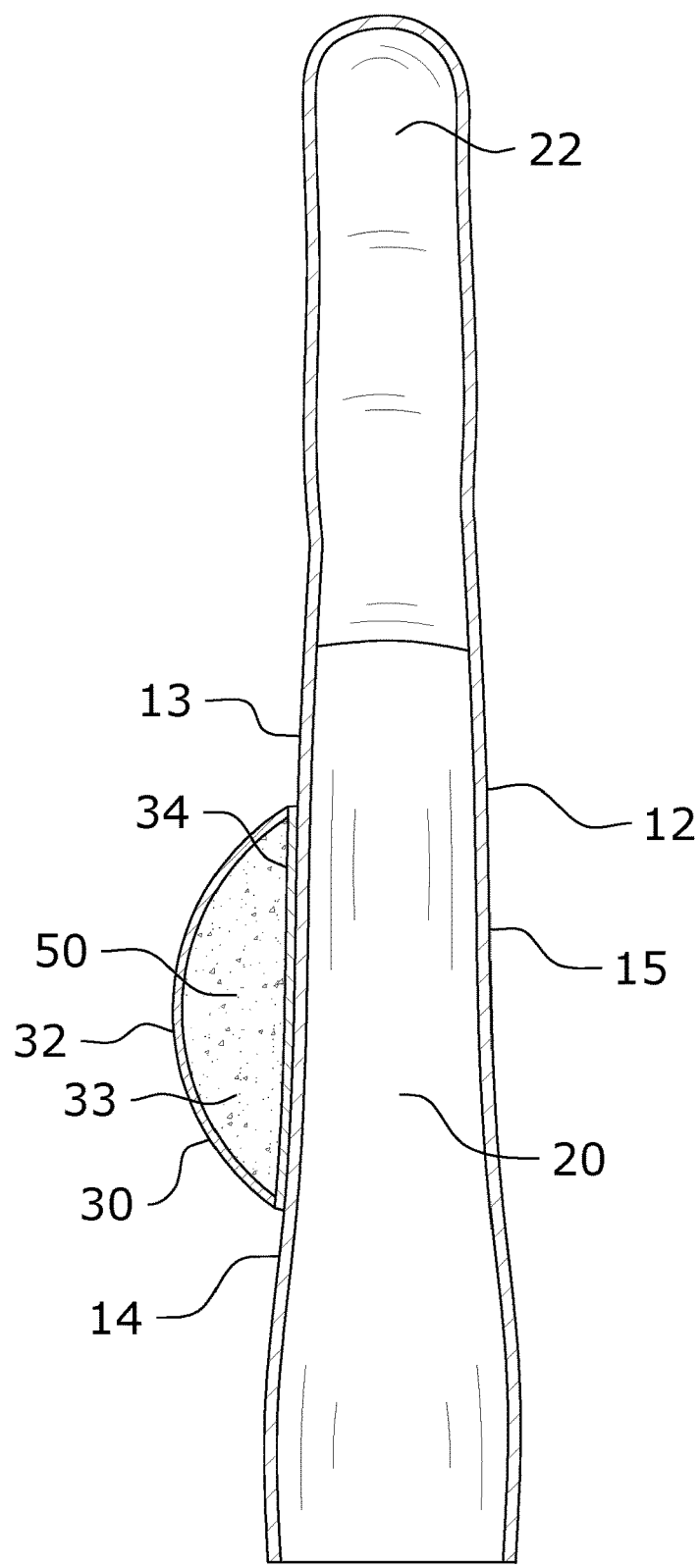
FIG. 5 is a cross-sectional view in accordance with the embodiment of FIG. 4.

FIGS. 4-5 depict an alternative embodiment in which the blister pack 30 is located on a palmar region 14 of the glove 12. Such a configuration may allow for a larger volume of a single hair product composition 50 to be contained within the blister pack 30 and dispensed by squeezing or applying pressure to the rupturable membrane 32 of the blister pack 30, which together with the backing sheet 34 that is at least partially in direct contact with the exterior surface 13 of the palmar region 14 of the glove 12 forms the pocket 33 that houses the hair product composition 50.

Figure 6:
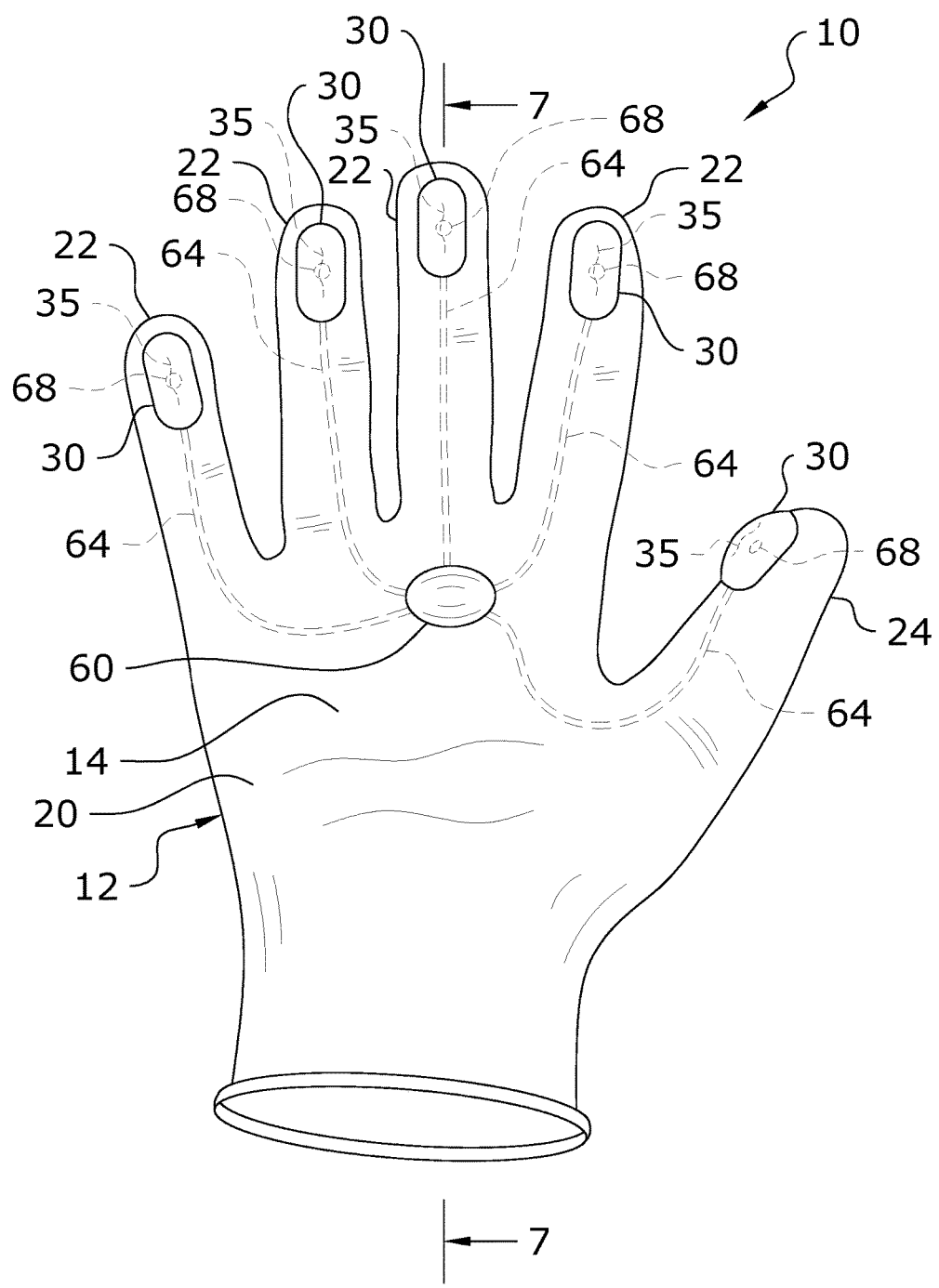
FIG. 6 is a palmar view of a hair product application device in accordance with an exemplary embodiment comprising a pneumatic device for dispensing a hair product.
Figure 7A:
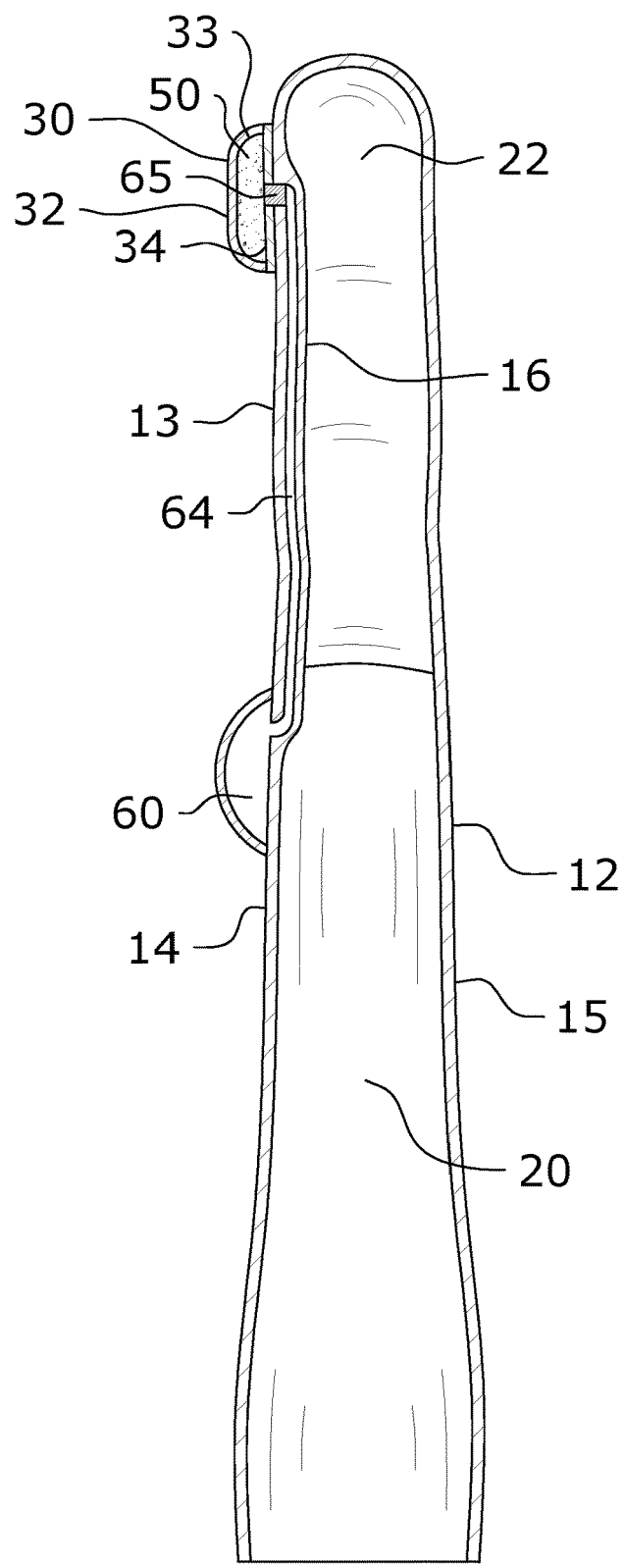
FIGS. 7A-B are cross-sectional views of a glove finger in accordance with the embodiment of FIG. 6.
Figure 7B:
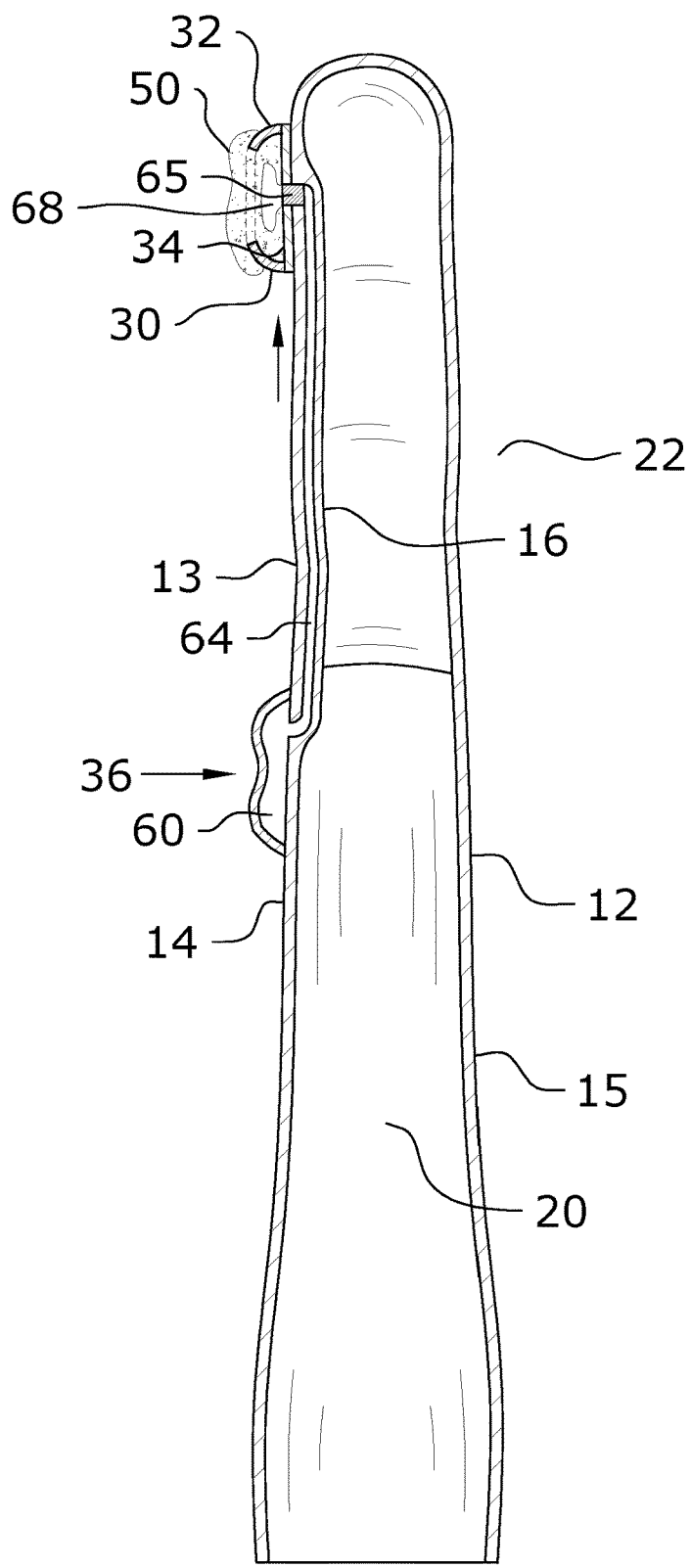

FIGS. 6-7B depict yet another alternative embodiment of a hair product application device 10. As shown, a pneumatic device 60 in fluid communication with one or more blister packs 30 via one or more tubes 64 may be used to create an internal pressure within the pocket 33 of the blister pack 30 to dispense a hair product composition 50. The pneumatic device 60 may, by non-limiting example, comprise a depressible bulb that functions as a pump to push air into the pocket 33 of one or more blister packs 30 to rupture the rupturable membrane 32. It is contemplated that any number of mechanisms and combinations of chambers, conduits, valves, pumps, etc. may comprise the pneumatic device 60 and its related components. As depicted in the cross-sectional views of FIGS. 7A-B, the one or more tubes 64 may be disposed between one or more external surface layers 13 of the glove 12 and one or more interior surface layers 16 of the glove 12 and the pneumatic device 60 may be integrally disposed to the glove 12. In this configuration, the tubes 64 are not visible and the smooth exterior surface 13 of the glove 12 is maintained which is desirable when applying the hair product composition 50 to a user's hair or scalp. While the pneumatic device 60 is shown here located on the palmar region 14 of the glove 12, the location is not limited as such and the pneumatic device 60 may be located anywhere on the glove 12 that allows for fluid communication between the pneumatic device 60 and the pocket 33 of the blister pack 30 via one or more tubes 64.

As shown in FIGS. 7A-B, the backing sheet 34 may comprise an opening or bore 65 through which the tube 64 fluidly communicates with the pocket 33 of the blister pack 30. When an external force 36 is applied to the pneumatic device 60, shown here as a depressible bulb, air that previously filled the pneumatic device 60 travels through the tube 64 and enters the pocket 33 of the blister pack 30 through the bore 65 in the backing sheet 34. This creates an increase in the internal pressure of the pocket 33 thereby causing the rupturable membrane 32 to rupture and dispense hair product composition 50. A one-way valve 68 may be located within the pocket 33 adjacent to the bore 65 to prevent hair product composition 50 from being pulled back into the tube 64. The one-way valve 68 may comprise a one-way ball valve, flapper valve, or any other suitable one-way valve.

Figure 8:
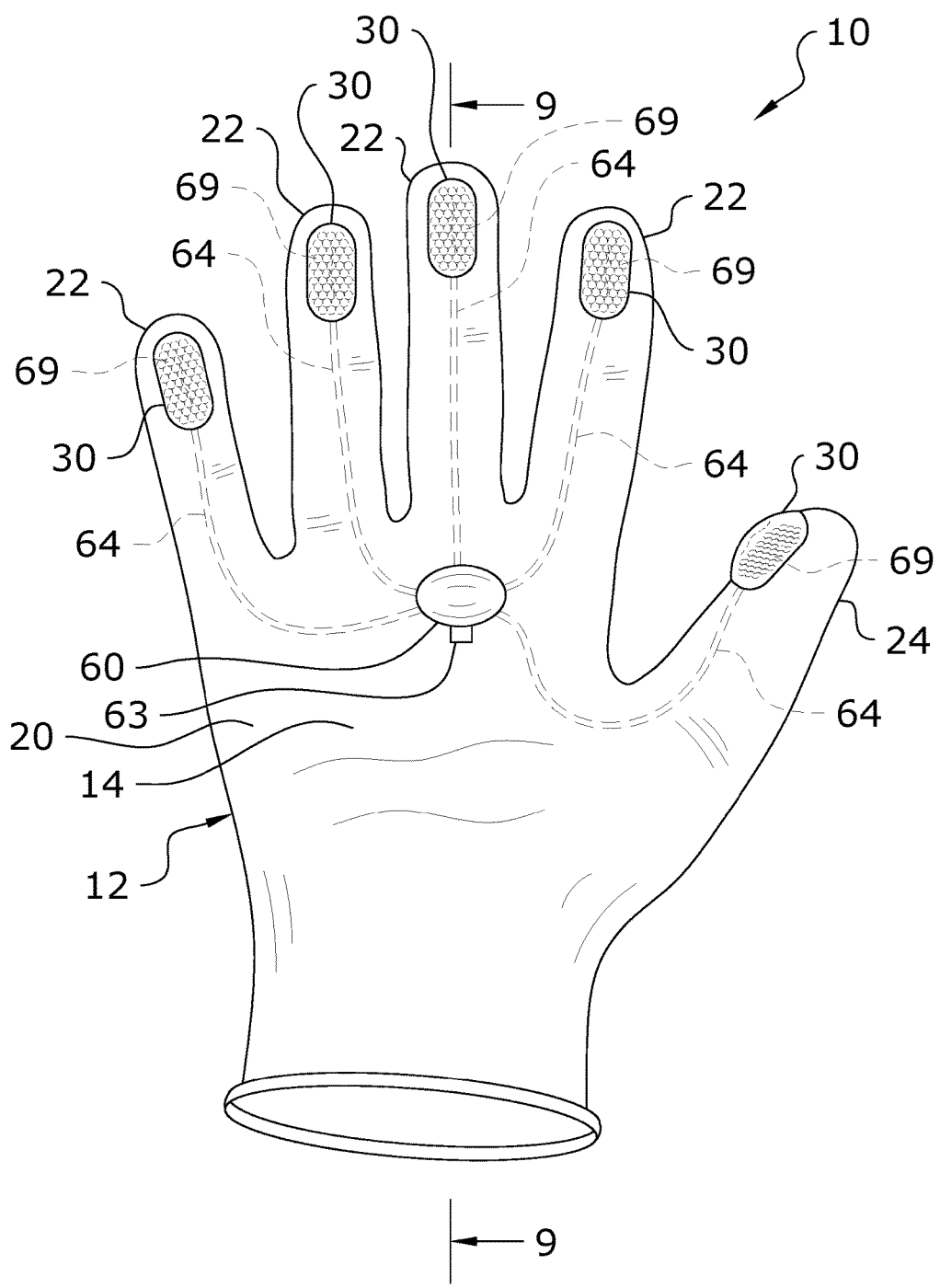
FIG. 8 is a palmar view of a hair product application device in accordance with an alternative exemplary embodiment comprising a pneumatic device for dispensing a hair product.
Figure 9A:
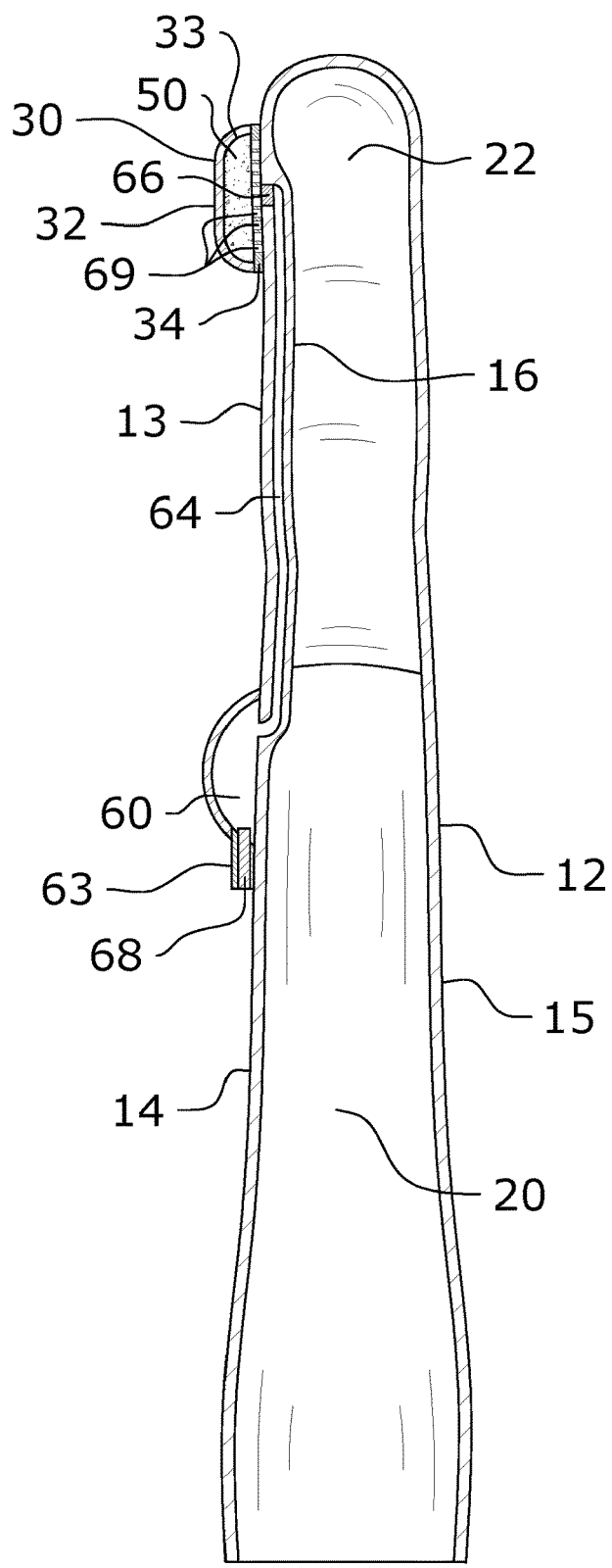
FIGS. 9A-B are cross-sectional views of a glove finger in accordance with the embodiment of FIG. 8.
Figure 9B:
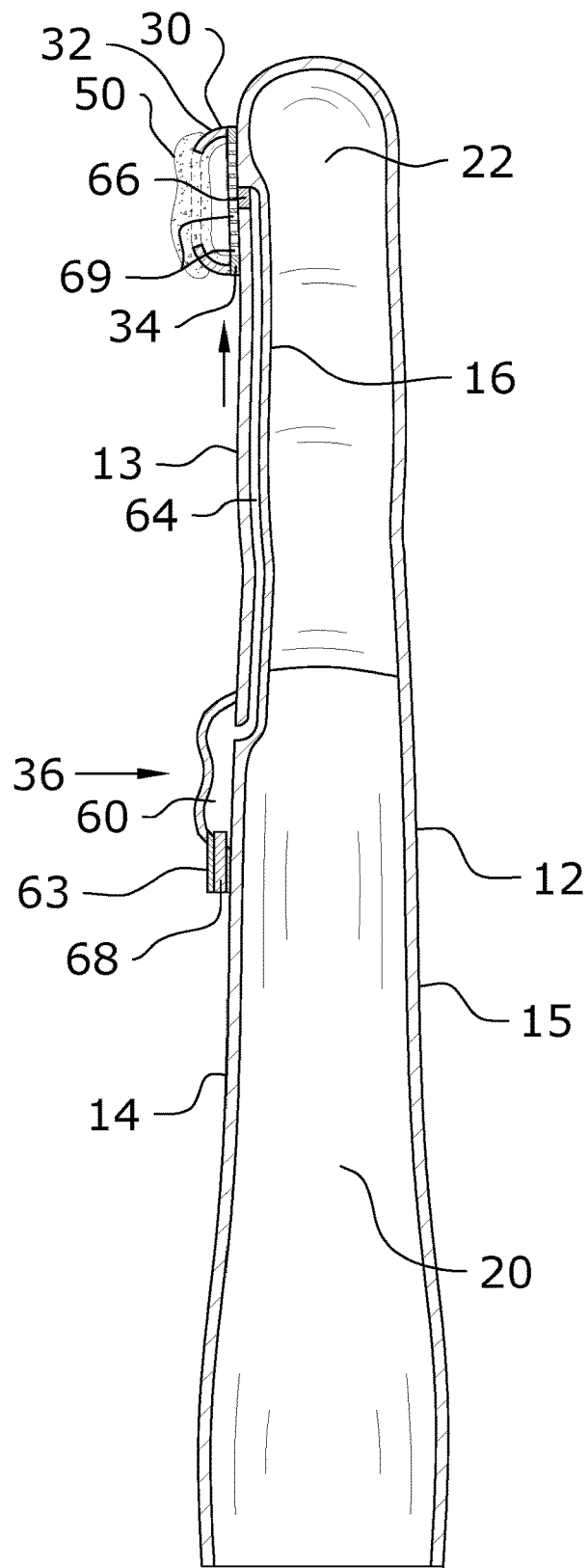

FIGS. 8-9B depict an alternative embodiment in which the tube 64 that is in fluid communication with the pneumatic device 60 and the pocket 33 is coupled to a tubular fitting 66 that fluidly communicates with a plurality of outlet ports 69 passing through a plurality of apertures in the backing sheet 34. When an external force 36 is exerted upon the pneumatic device 60, air that previously filled the pneumatic device 60 travels through the tube 64 and tubular fitting 66 and enters the pocket 33 of the blister pack 30 through the plurality of outlet ports 69 in the backing sheet 34. This creates an increase in the internal pressure of the pocket 33 thereby causing the rupturable membrane 32 to rupture and dispense hair product composition 50. The pneumatic device 60 may further comprise an inlet 63 through which air may enter the pneumatic device 60. The inlet 63 may further comprise a one-way valve 68 to prevent previously dispensed hair product composition 50 from entering the pneumatic device 60 through the inlet 63.

Figure 10:
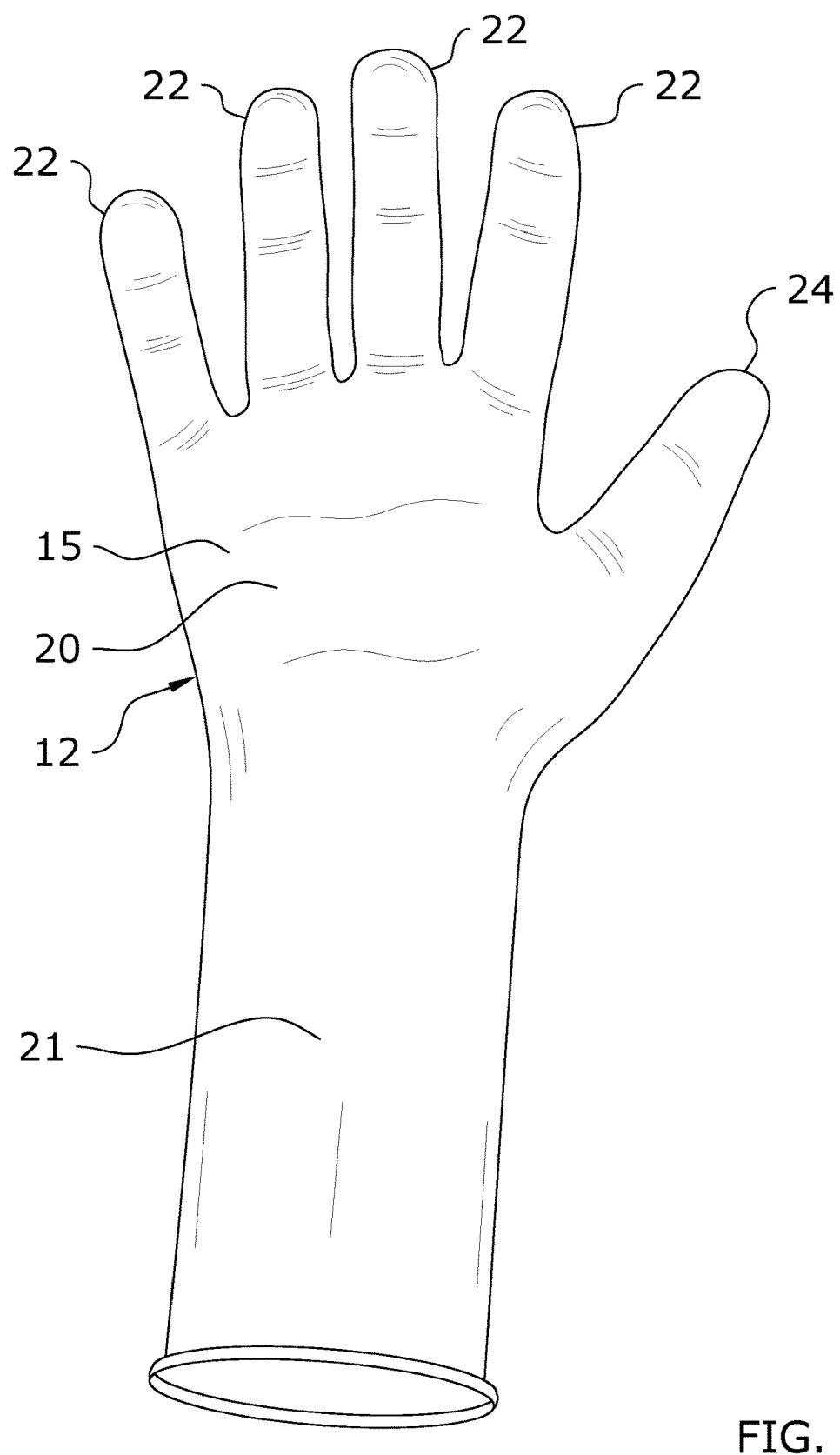
FIG. 10 is a dorsal view of a hair product application device in accordance with an exemplary embodiment having an elongated glove sleeve.

FIG. 10 provides a dorsal view of an exemplary embodiment of the hair product application device 10 comprising an elongated sleeve portion 21 that may provide enhanced protection of the user's arm to prevent exposure to dyes and other harmful chemicals during application of one or more hair products.

Figure 11:
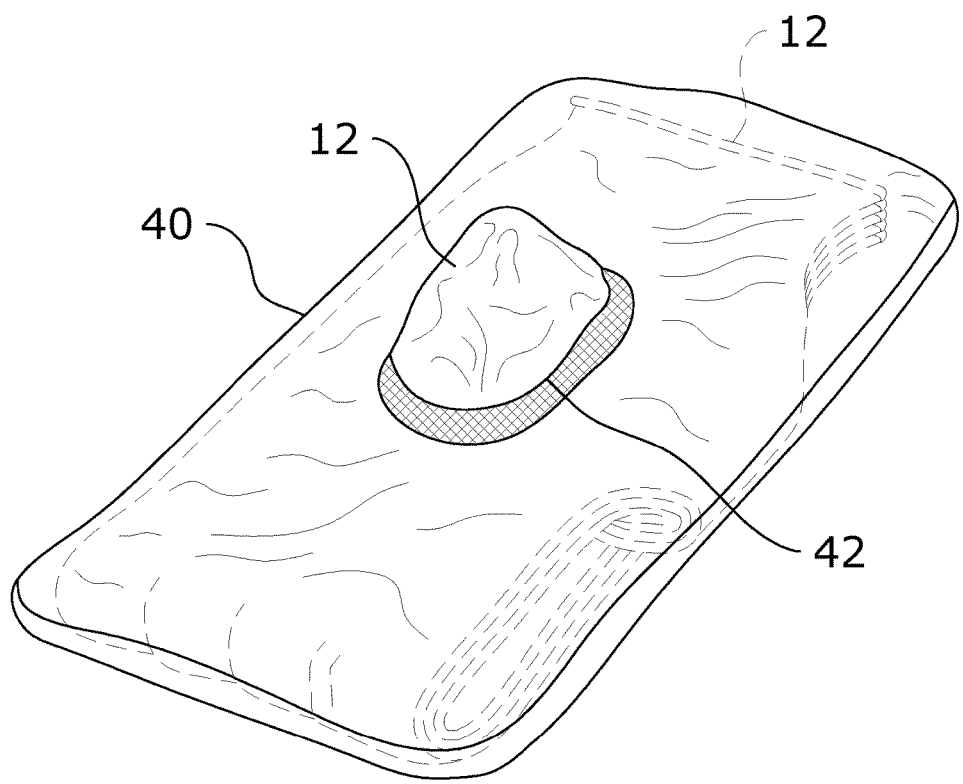
FIGS. 11-12 are perspective views of exemplary embodiments of a dispenser for a hair product application device.
Figure 12:
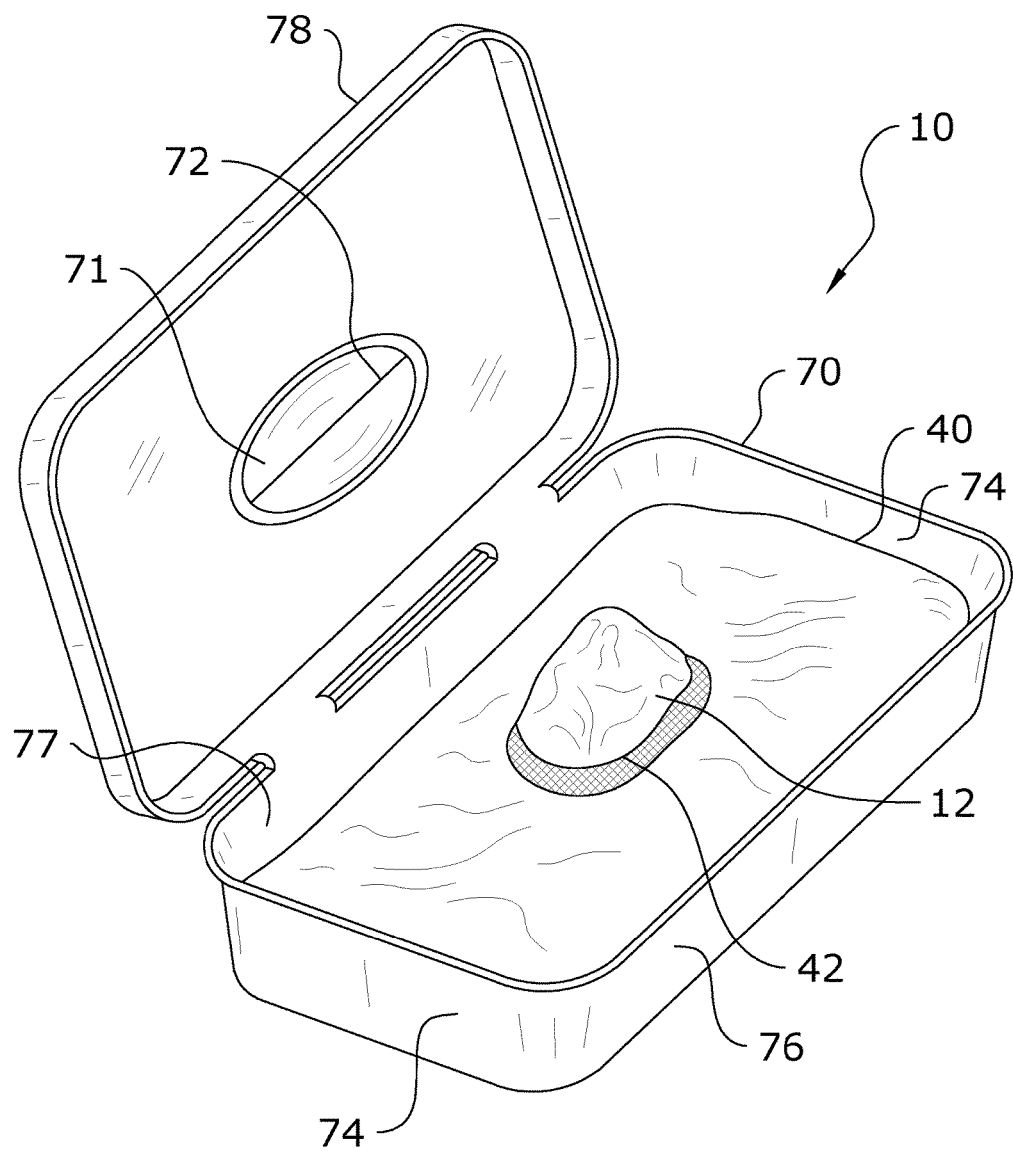

Additionally, any of the embodiments described herein may be stored in and dispensed from the exemplary embodiments of a hair product application device dispenser as depicted in FIGS. 11-12. These dispensers are particularly useful when the hair product application device 10 comprises a disposable glove 12. FIG. 11 depicts a pouch 40 which may be comprised of a lightweight material such as a plastic or more specifically a low density plastic polymer material such as a low density polyethylene, polypropylene, or other similar materials. A plurality of gloves 12 may be nested or stacked inside the pouch 40 and the pouch 40 may be sized to conveniently fit within a user's garment pocket, purse, or other receptacle that facilitates ease of use. The pouch 40 may comprise a sealed, openable slit 42 located anywhere on a surface of the pouch which may be opened and spread apart to allow removal of one or more gloves 12.

As shown in FIG. 12, the hair product application device 10 may also be dispensed from a rigid or semi-rigid dispenser container 70 which may contain a pouch 40 in which a plurality of gloves 12 are nested or stacked for dispensing through an openable slit 42. The container 70 may comprise an enclosed structure having a front wall 76, a rear wall 77, and opposing side walls 74 extending upward from a bottom wall. The container 70 may comprise a lid 78 pivotally coupled to the rear wall 77 using one or more hinges which may, for example, be thermoformed during manufacturing. The lid 78 may comprise a window 71 which may be centrally-positioned on the lid 78 (shown in FIG. 12 as oval-shaped, although any suitable shape is contemplated). Within the window 71 is a lid slit 72 which is configured to align with the openable slit 42 of the pouch 40 when the lid 78 of the container 70 is in a closed position so that a user may pass a glove 12 from the pouch 40 through the lid slit 72. The container 70 may be comprised of any suitable material such as a plastic, or preferably, from 20 gauge polystyrene or any other heat formable material such as polyvinyl chloride or polyethylene that may be easily and inexpensively manufactured using known techniques such as thermoforming and injection molding.

The hair product composition 50 comprises formulations that are ideally suitable for various hair care treatments such as, by non-limiting example, shampoos, pomades, grease mixtures, styling gels, mousses, relaxers, straighteners, detanglers, conditioners, emollients, coloring agents, and any other suitable hair or scalp treatment product. Thus, an additional advantage provide by at least some of the embodiments disclosed herein is that a user may utilize one or more hair product compositions 50 from multiple blister packs 30 located on a single glove 12 or pair of gloves 12 during a single hair care treatment event. In accordance with an exemplary method of using the hair product application device 10, a glove 12 or pair of gloves 12 having a plurality of blister packs 30 may be selected and placed on the hand(s) of a user. The user may then rupture a first blister pack 30 by creating a pressure differential between the interior rupturable membrane surface 37 and the exterior rupturable membrane surface 38 according to any of the embodiments previously discussed in this disclosure. The user may then apply the resultant released hair product composition 50 to the user's or to another individual's hair or scalp. If desired, the user may then rupture a second blister pack 30 containing the same or a different hair product composition 50 for additional application. This process may be repeated to dispense and apply as many hair product compositions 50 as desired by the user. For example, a user may accomplish an efficient application of multiple products such as a pretreatment relaxer followed by a relaxer composition without needing to change gloves or utilize bottles or other dispensing mechanisms for the various hair product compositions 50.

In accordance with one embodiment, the hair product composition 50 comprises at least one of a shampoo or detangling formulation, the composition comprising one or more of the following agents: ammonium lauryl sulfonate, triethanolamine, lauramide DEA, lecithin, glycol stearate, methylparaben, methylisothiozoline, water, ammonium laureth sulfate, ammonium lauryl sulfate, glycol distearate, dimethicone, cocamide MEA, cetyl alcohol, fragrance, polymethacrylamidopropyl, trimonium chloride, sodium citrate, DMDM hydantoin, sodium chloride, PEG-14M, dehydrogenated tallowmideothyl hydroxyethylmonium, disodium EDTA, phenoxyethanol, citric acid, methyldibromoglutaronitrile, ammonium xylene-sulfonatem, various coloring agents, 2-oleamido-1,3-octadecanediol (ceramide-r), acetamide MEA, acrylates/C10-30 alkyl acrylate crosspolymer, acrylic acid polymer (carbomer 1342), alcohol, aloe vera gel, aluminum starch octenylsuccinate, amodimethicone, arginine, benzophenone-3, benzophenone-4, biotin, butylated hydroxytoluene, butylene glycol, butylparaben, carbomer, carboxylic acid, cetrimonium chloride, chloroxylenol, coal tar distillate, cocamide DEA, cocamide MIPA, cocamidopropyl betaine, cocamidopropyl hydroxysultaine, cocamidopropylamine oxide, cocobetaine, cocodimonium hydroxypropyl hydrolyzed hair keratin, cocotrimonium chloride, cyclomethicone, cysteine, DEA-methoxycinnamate, decyl polyglucose, diazolidinyl urea, dimethiconol, dimethyl ether, disodium cocoamphodiacetate, disodium laureth sulfosuccinate, disodium lauroamphodiacetate, disodium oleamido MEA sulfosuccinate, disodium phosphate, disodium ricinoleamido, ergocalciferol, ethylparaben, glycerin distearyldimonium chloride, glycerin, glycol stearate, glycosaminoglycans, guar hydroxypropyltrimonium chloride, hydrochloric acid, hydrolyzed animal protein, hydrolyzed collagen, hydrolyzed keratin, hydrolyzed silk, hydrolyzed vegetable protein, hydrolyzed wheat protein, hydrolyzed wheat starch, hydrolyzed yeast, hydroxypropyl guar hydroxypropyltrimonium chloride, hydroxypropyl methylcellulose, hydroxypropyltrimonium hydrolyzed wheat protein, imidazolidinyl urea, inositol, iodopropyl butylcarbamate, iodopropynyl butylcarbamate, isobutene, isolaureth-6, isostearamidopropyl moorpholine lactate, keratin amino acids, ketoconazole, lactamide MEA, lauramide DEA, lauramphoglycinate, laureth-10, laureth-23, laureth-4, laureth-6, lauryl alcohol, lecithin, magnesium citrate, magnesium laureth sulfate, measulfosuccinate, menthol, methenamine, methoxypropylgluconamide, methylcholoroisothiazolinone, methylisothiazolinone, methylparaben, mica, octoxynol-40, octyl Dimethyl PABA, octyl hydroxystearate, octyl methoxycinamate, olealkonium chloride, palmitic acid, pantethine, panthenol, panthenyl ethyl ether, pantothenic acid, PEG-12, PEG-120 methyl glucose dioleaste, PEG-15, coco polyamine, PEG-150 distearate, PEG-23M, PEG-27 lanolin, PEG-55 propylene glycol oleate, PEG-50 almond glycerides, PEG-600, PEG-7 glyceryl cocoate, PEG-80 sorbitan laurate, phosphoric acid, phytantriol, phytic acid, polyquaternium-16, polyquaternium-10, polyquaternium-4, polyquaternium-11, polyquaternium-46, polyquaternium-30, polyquaternium-7, polysorbate 20, polysorbate 80, potassium cocoyl hydrolyzed collagen, potassium sorbate, PPG-12 buteth-16, PPG-5 laureth 5, PPG-9, propylene glycol, proplyparaben, pyrithione zinc, quaternium-15, quaternium-22, quaternium-75, quaternium-80, retinyl palmitate, ricinoleamidopropyl ethyldimonium ethosulfate, SD alcohol 40, serum protein, silk amino acids, silk protein, silsesquioxane copolymer, sodium benzoate, sodium C14-17 alkyl SEC sulfonate, sodium cocoyl sarcosinate, sodium glutamate, sodium hydroxide, sodium hydroxymethyglycinate, sodium laureth sulfate, sodium laureth-13 carboxylate, sodium lauriminodipropionate, sodium lauroyl sarcosinate, sodium lauryl sulfate, sodium methylparaben, sodium myreth sulfate, sodium oleth sulfate, sodium phosphate, sodium styrene/acrylates/divinylbenzene copolymer, sodium sulfate, sodium trideceth sulfate, solubilized coal tar extract, soluble collagen, soyamide DEA, stearyl alcohol, talloweth-60 myristyl glycol, TEA-dodecylbenzenesulfonate, TEA-dodecylphenylsulfonate, TEA-lauryl sulfate, tetrasodium EDTA, tissular fluid extract, titanium dioxide, tocopheryl acetate, topical tar solution, trideceth-12, triethanolamine lauryl sulfate, trimethylsilylamodimethicone, wheat oligosaccharides, wheatgermamidopropyl, dimethylamine, xanthan gum, yeast extract, hydrolyzed soy protein, sodium PCA, ethoxydiglycol, linoleamidopropyl PG-dimonium chloride phosphate, hydrogenated polydecene, trimethylolpropane, phenoxyethanol and various fruit, mineral and vitamin extracts.

In accordance with one embodiment, the hair product composition 50 comprises a at least one of a styling gel or a mousse formulation, the composition comprising one or more of the following agents: acetamide MEA, acrylate copolymer, acrylates/dimethicone/methacrylate copolymer, alanine, alcohol denat, allantoin, aminoethylpropanol, aminomethyl propanol, ammonium benzoate, ammonium hydroxide, amodimethicone, arachidonic acid, arginine, ascorbyl palmitate, behenic acid, benzophonone-3, benzophenone-4, betaine, boric acid, butyl ester of PVM/MA copolymer, C13-14 isoparaffin, calcium pantothenate, carbomer, carbopol, catalase, cetearyl octanoate, ceteth-16, ceteth-20, cetrimonium bromide, cetrimonium chloride, cetyl alcohol, chlorhexidine dihydrochloride, cocamide DEA, cocamidopropyl betaine, cocamidopropyl hydroxysultaine, collagen, cyclomethicone, DEA-methoxycinnamate, diazolidinyl urea, diisobutyl adipate, dimethicone copolyol, dimethiconol, dimethyl ether, dimethyl lauramine isostearate, dimethyl stearamine, dioctyl sebacate, distearlydimonium chloride, ethosulfate, ethyl ester of PVM/MA copolymer, ethyldimonium, gelatin, glutamic acid, glycerin, glycine, hyaluronic acidm, hydrofluorocarbon 152A, hydrolyzed elastin, hydrolyzed soy protein, hydrolyzed wheat protein, hydrolyzed wheat starch, hydrophilic polyether polyurethane, hydroxyethyl cellulose, hydroxypropyl guar, hydroxypropyl methylcellulose, iodopropynyl butylcarbamate, isododecane, isopropyl alcohol, isosteareth-10, keratin protein, lactamide MEA, laneth-16, lauramide DEA, lauramide MEA, laureth-11, laureth-23, laureth-4, laureth-7, laureth-9, lecithin, linoleamidopropyl, linoleic acid, lysine, lysine hydroxypropyl trimonium chloride, methylchloroisothiazolinone, methylchloroisothiazolinone, methylchloroisothiazoline, methylisothiazoline, methylisothiazolinone, methylparaben, mineral oil, myristoyl hydrolyzed collagen, niacinamide, SD alcohol 40, nonoxynol-10, octyl hydroxystearate, octyl salicylate, octylacrylamide/acrylates copolymer, octylacrylamide/acrylates/butylaminoethyl meth, octoylmethoxycinnamate, olealkonium chloride, oleic acid, oleth 20, oleth-16, palmitic acid, palmitoyl myristyl serinate, PEG-15 cocamine chloride, PEG-40 hydrogenated castor oil, PEG-6 cocamide, PEG-60 hydrogenated castor oil, PEG-75 lanolin, PEG-8 sorbitol, phenoxyethanol, phenyl trimethicone, phospholipids, phytantriol, polyacrylamide, polyquaternium-11, polyquaternium-46, polyquaternium-7, polysorbate 20, polysorbate 80, polyzophenone-4, potassium dimethicone copolyol panthenyl phosphate, potassium hydroxide, potassium sorbate, PPG-12-PEG-50 lanolin, PPG-5-ceteth-20, PPG-9 diethylmonium chloride, proline, PVP, pyridoxine NCL, quaternium-15, retinyl palmitate, ribonucleic acid, serine, silk amino acids, silk protein, sodium benzoate, sodium C13-15 pareth-8 butyl phosphate, sodium C13-15 pareth-8 phosphate, sodium C14-16 olefin sulfonate, sodium chloride, sodium cocoyl isethionate, sodium hydroxymethylglycinate (amino acid derived), sodium PCA, sorbitol, soyamide DEA, stearalkonium chloride, steareth-16, steareth-2, stearic acid, stearyl alcohol, tea-dodecylbenzenesulfonate, tetrasodium EDTA, threonine, tocopheryl acetate, trideceth-12, triethanolamine, trisopropanolamine, urethane/C1-C20 peg alkyl copolymer, VA/crotonates/vinyl neodecandate copolymer, various fruit, plant, vitamin extracts, wheat germamidopropyl ethyldimonium ethosulfate, yeast extract, isobutane, AMP-isostearoyl hydrolyzed soy protein, butylene glycol, and SD alcohol 40.

In accordance with one embodiment, the hair product composition 50 comprises a at least one of a relaxer or a straightener formulation, the composition comprising one or more of the following agents: emulsifying wax, petrolatum, PPG-12-PEG-50 lanolin, PEG-75 lanolin, steareth-21, steareth-10, polysorbate-60, mineral oil, propylene glycol, water, calcium hydroxide, xanthan gum, guanidine carbonate, calcium, magnesium, and a metal ion chelating agent, the metal ion chelating agent selected from the group consisting of ethylenediaminetetraacetic acid, diethylenetriaminepentaacetic acid, hydroxyethylethylenediaminetriacetic acid, nitrilotriacetic acid, ethanol diglycine, ethylenebis(hydroxyphenylglycine), N-dihydroxyethylglycine, iminodisuccinic acid, ethylenediaminedisuccinic acid, polyaspartic acid, and water soluble alkali metal salts thereof, employed singly or in combination.

It is to be understood that the embodiments and claims are not limited in application to the details of construction and arrangement of the components set forth in the description and/or illustrated in drawings. Rather, the description and/or the drawings provide examples of the embodiments envisioned, but the claims are not limited to any particular embodiment or a preferred embodiment disclosed and/or identified in the specification. Any drawing figures that may be provided are for illustrative purposes only, and merely provide practical examples of the invention disclosed herein. Therefore, any drawing figures provided should not be viewed as restricting the scope of the claims to what is depicted.

The embodiments and claims disclosed herein are further capable of other embodiments and of being practiced and carried out in various ways, including various combinations and sub-combinations of the features described above but that may not have been explicitly disclosed in specific combinations and sub-combinations.

Unless otherwise defined, all technical and scientific terms used herein have the same meaning as commonly understood by one of ordinary skill in the art to which this invention belongs. Although methods and materials similar to or equivalent to those described herein can be used in the practice or testing of the hair product application device, suitable methods and materials are described above. All publications, patent applications, patents, and other references mentioned herein are incorporated by reference in their entirety to the extent allowed by applicable law and regulations. The hair product application device may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

What is claimed is:
1. A hair product application device consisting of:
a glove comprising a plurality of digit portions; and
a blister pack disposed on at least one digit portion from among the plurality of digit portions, the blister pack consisting of:

a pocket containing a hair product composition, the pocket located on at least a portion of an exterior surface of the at least one digit portion of the glove; and a rupturable membrane at least partially forming the pocket and configured to release at least a portion of the hair product composition when ruptured in response to a pressure differential between an internal pressure exerted on the rupturable membrane and an external pressure exerted on the rupturable membrane.

2. A hair product application device consisting of:

a glove; and a blister pack disposed on an exterior surface of the glove, the blister pack consisting of:

a pocket containing a hair product composition, the pocket located on at least a portion of an exterior surface of the glove; and a rupturable membrane at least partially forming the pocket and configured to release at least a portion of the hair product composition when ruptured in response to a pressure differential between an internal pressure exerted on the rupturable membrane and an external pressure exerted on the rupturable membrane.

3. The hair product application device of claim 2, wherein the blister pack is located on at least one of a palmar region, a dorsal region, and a digit portion of the exterior surface of the glove.

4. A method of using a hair product application device comprising:

placing a glove consisting of a blister pack on an exterior surface of the glove onto a hand of a user, wherein the blister pack consists of a pocket containing a hair product composition and a rupturable membrane;

creating a pressure differential between an internal pressure exerted on the rupturable membrane and an external pressure exerted on the rupturable membrane of-the pocket which is located at least partially in direct contact with the exterior surface of the glove;

rupturing the rupturable membrane in response to the pressure differential such that the hair product composition is released from the pocket; and applying the hair product composition to hair of the user or another individual.

5. The method of claim 4, further comprising removing a removable cover from over the rupturable membrane prior to creating the pressure differential.

6. The method of claim 4, wherein creating the pressure differential comprises applying a force to an external surface of the rupturable membrane.

* * * * *